United States Patent [19]

Tsurumizu et al.

[11] Patent Number: 4,661,350
[45] Date of Patent: Apr. 28, 1987

[54] DENTAL VACCINE FOR INHIBITING PERIODONTITIS

[75] Inventors: Takashi Tsurumizu, Chiba; Takashi Hashimoto; Takashi Takahashi, both of Tokyo, all of Japan

[73] Assignee: Kitasato Kenkyusho, Tokyo, Japan

[21] Appl. No.: 881,864

[22] Filed: Jul. 3, 1986

Related U.S. Application Data

[63] Continuation of Ser. No. 558,257, Dec. 5, 1983, abandoned.

[30] Foreign Application Priority Data

Dec. 8, 1982 [JP] Japan .................. 57-215146

[51] Int. Cl.$^4$ ............... A61K 39/07; A61K 39/02; A61K 39/116
[52] U.S. Cl. ..................... 424/92; 435/253; 435/822; 435/826
[58] Field of Search ............ 424/92; 435/253, 822, 435/826

[56] References Cited

U.S. PATENT DOCUMENTS

| | | | |
|---|---|---|---|
| 4,268,434 | 5/1981 | Higerd et al. | 435/826 X |
| 4,287,173 | 9/1981 | Carlo et al. | 424/92 X |
| 4,442,085 | 4/1984 | Colman et al. | 424/92 X |
| 4,472,302 | 9/1984 | Karkhanis | 260/112 R |

OTHER PUBLICATIONS

J. Periodontal Res. 14:453–466, (1979), Hunter et al.

*Primary Examiner*—Howard E. Schain
*Attorney, Agent, or Firm*—Wolder, Gross & Yavner

[57] ABSTRACT

A vaccine for preventing or at least inhibiting periodontitis of humans and animals, which is induced or deteriorated by the action of oral microorganisms, which comprises an antigen isolated from the pili of an oral microorganism capable of inducing and/or deteriorating periodontitis and having the pili on the cell surface. For example, antigens isolated from the pili of *Actinomyces viscosus, Actinomyces naeslundii, Actinobacillus actinomycem comitans, Bacteroides gingivalus* and mutant strains thereof may be used solely or in combination for the preparation of the present vaccine. In one embodiment, the vaccine comprises an antigen isolated from the pili of *Actinomyces viscosus* which is a representative periodontitis-inducing oral microorganisms in association with one or more other antigens isolated from other virulent oral microorganisms. The antigen isolated from the pili may effectively inhibit the adherence (infection) of the virulent oral microorganisms of at least same species to the surfaces of teeth and/or mucous membrane of an oral cavity.

8 Claims, No Drawings

DENTAL VACCINE FOR INHIBITING PERIODONTITIS

This application is a continuation of application Ser. No. 558,257, filed Dec. 5, 1983, now abandoned.

BACKGROUND OF THE INVENTION

The present invention relates broadly to vaccines and more particularly relates to a dental vaccine for preventing or at least inhibiting periodontitis.

In this specification, the term periodontitis denotes a wide variety of diseases of humans and animals, which occur in the periodontal area of the oral cavity such as, for example, gingiva (gum), cementum and alveolar bone. It may in general be classified into the marginal periodontitis exemplified by pyorrhoea alveolaris and the apical periodontitis. Various known etiological factors of periodontitis include biological activities of virulent bacilli in the oral floras, such as, for example, the formation of dental plaque on the surface of teeth and the formation of cyst in the periodontal tissues, which breaks down the periodontal tissue. Such virulent oral bacilli are exemplified by *Actinomyces viscosus, Actinomyces naeslundii, Bacteroides gingivalus, Actinobacillu actinomycetemcomitans* and the like. Among them, *Actinomyces viscosus* is most important because this microorganism produces from sucrose a large amount of levan-type polysaccharides which greatly adhere to the surface of teeth. Although the periodontitis-inducing activities of other virulent bacilli are not necessarily stronger than the activity of *Actinomyces viscosus*, it is sometimes observed in practice that these microorganisms are capable of deteriorating periodontitis in coexistence with *Actinomyces viscosus*. Also, it is often found that the above-mentioned oral bacilli form a majority of the oral bacilli present in the focus of periodontitis.

Various proposals have hitherto been made to treat human periodontitis. However, to our knowledge, no vaccine for treating periodontitis is known in the art. On the other hand, it was previously known that, for example, the above-mentioned periodontitis-inducing oral bacilli possess the pili (fimbriae) on their cell surfaces, by the action of which they are capable of adhering (infecting) to the surfaces of teeth and/or the mucous membrane in the oral cavity. However, the antigenic characteristics of the pili of such virulent oral bacilli have not yet been clarified in view of etiological factors of periodontitis.

It has now unexpectedly been discovered that an antigen isolated from the pili of a periodontitis-inducing microorganism is capable of preventing or at least inhibiting the adherence (infection) of the microorganisms of at least same species to the surfaces of teeth and/or mucous membrane in an oral cavity.

SUMMARY OF THE INVENTION

An object of the present invention is to provide a vaccine for preventing or at least inhibiting priodontitis which is induced or deteriorated by the action of periodontitis-inducing oral bacilli having the pili on the cell surface.

According to the present invention, there is provided a vaccine for preventing or at least inhibiting periodontitis which is induced or deteriorated by the action of oral microorganisms, which comprises as antigen at least one pili component antigen in association with a physiologically acceptable carrier.

The term pili component antigen used herein denotes an antigen isolated from the pili of an oral microorganism capable of inducing and/or deteriorating peridontitis and having the pili on the cell surface (hereinafter referred to as virulent oral microorganims).

By immunizing humans and animals with the pili component antigen of the present invention, it is possible with advantage to prevent or at least inhibiting periodontitis which is induced or deteriorated by the action of virulent oral microorganisms of at least same species.

PREFERRED EMBODIMENTS

For the purpose of the present invention, the pili of any and all virulent oral microorganisms (as hereinbefore defined) such as, for example, *Actinomyces viscosus, Actinomyces naeslundii, Actinobacillus actinomycetem comitans, Bacteroides gingivalus* and the like may be used. Although *Actinomyces viscosus* is most important, they may be used solely or in combination, and various mutant strains thereof may also be used for the purpose of the present invention insofar as they are capable of inducing or deteriorating periodontitis. Thus, if desired, the present vaccine may comprises two or more pili component antigens originating from virulent microorganisms of different species.

In the examples and experiments described hereinafter, *Actinomyces viscosus* Mutant Strain K-TL+ (FERM-BP 411) and *Bacteriodes gingivalus* Strain K-Bg-ml (FERM-BP 410) are used. *A. viscosus* Mutant Strain K-TL+ is a mutant strain presently induced from a corresponding wild strain. Where this mutant strain is cultured, for example, by using a TYC medium, TYC agar plate medium and the like, a large amount of levan-type polysaccharides is produced by decomposing sucrose. Where this strain is cultured in a liquid medium, a large amount of the grown cells adheres massively to tube wall. Where this strain is subcultured over an extended period of time in various media or treated with various known mutagents such as, for example, nitrosoguanidine, nitrogen mustard, irradiation of ultraviolet rays and the like, it has been observed that this strain is genetically stable so that any reversion to its parent strain and generation of any other mutant strain do not occur. By oral administration of this strain to hamsters, this strain adheres well to the surfaces of teeth and mucous membrane in the oral cavity. Where the animals are bred with a cariogenic diet, the presence of a strong periodontitis-inducing activity has been noted with reference to the resorption of the alveolar bone.

*Bateroides gingivalus* Strain K-Bg-ml is a wild strain selected from many wild strains isolated from human periodontitis with reference to a stronger reactivity with hemoagglutinin and a higher adhering ability to the cells. In comparison with other wild strains of the same species, this strain is characterized by its stronger adhering ability to the epithelial cells of the mucous membrane in the oral cavity and stronger reactivity for hemoagglutinin. Where this strain is orally administered to hamsters, its adhering ability is not necessarily very strong. However, where, for example, *Actinomyces viscosus* Mutant Strain K-TL+ (FERM-BP 411) has been infected to hamsters and then *B. gingivalus* Strain K-Bg-ml is orally infected immediately before or after the beginning of the symptoms of periodontitis, it has been observed that this wild strain adheres well. Moreover, a considerably stronger periodontitis may be induced owing to such a mixed infection in comparison with the sole function of *Actinomyces viscosus* Mutant Strain K-TL+.

The mycological characteristics of two microorganisms are as follows:

(A) *Actinomyces viscosus* Mutant Strain K-TL+ (FERM-BP 411)
 I. Morphology: Rod, Gram-positive, $1 \times 3$–$4\mu$,
 II. Growth property: Anaerobic (faculative aerobic).
 III. Growth on various media:
  (1) TYC agar plate medium [pH about 7.2; Stoppelaar et al, Arch. Oral Biol., 12, 1199–1201 (1967)]: Colonies formed are rough, raised, grainy, mucoid, white and solid, and covered with abundant levan-type polysaccharides. Margins are irregular.
  (2) Brain-heart infusion agar plate medium [pH about 7.4; in 9 cm dish; commercial product of Baltimore Biological Laboratories Inc., U.S.A. hereinafter referred to as BBL]: Colonies are round, colorless, thick and translucent and have uniform and smooth surfaces and regular margins.
  (3) Tryptocase soy broth [pH about 7.8; BBL]: Growing from the lower layer of the medium.
  (4) Todd Heuwitt broth [pH about 7.8; BBL]: Growing from the lower layer of the medium.
 IV. Physiological characteristics:
  (1) Production of levan-type polysaccharides: +++
  (2) Adhering ability to tube wall: +++
  (3) Formation of pigment: negative
  (4) Growth range: pH=6–8.5. temperature=22°–39° C.
  (5) Decomposition of sugars: adonite, arabinose and dextrin . . . negative; furctose and galactose . . . +; glucose, inulin and lactose . . . negative; maltose, mannitol, mannose, mellibiose, raffinose and sucrose . . . +; xylose . . . negative.
 V. Miscellaneous: catalase . . . +; indol . . . negative; reduction of nitrate . . . +; production of hydrogen sulfide . . . +; liquefaction of gelatin . . . negative; hydrolysis of esculin . . . +; adhersion to the epithelium of oral mocus membrane . . . ++.
 VI. Induction of periodontitis: Induction of periodontitis . . . +++ (determined with reference to the resorption of the alveolar bone).

(B) *Bacteroides gingivalus* Strain K-Bg-ml (FERM-BP-410)
 I. Morphology: Gram-positive rod, $0.5 \times 0.8\mu$.
 II. Growth property: Obligatory ananerobic
 III. Growth on various media:
  (1) 10% blood agar plate medium [pH about 7.3; BBL]: Colonies are round, large, flat, somewhat bright and black and have smooth surfaces and margins. No hemolysis.
  (2) Bacteroides agar plate medium [pH about 7.2; in 9 cm dish; commercial product of Nissui Seiyaku K.K., Japan]: Round, somewaht smaller, flat, uniform and transparent colonies having smooth surfaces and margins.
  (3) Tryptocase soy broth [pH about 7.8; BBL]: Growing from the lower layer of the medium.
 IV. Physiological characteristics:
  (1) Formation of pigment: negative.
  (2) Growth range: pH=5.0–8.5. temperature=22°–39° C.
  (3) Decomposition of sugars; adonite, arabinose, dextrin, fructose, galactose, glucose, inulin, lactose, mannitol, mannose, mellibiose, raffinose and sucrose . . . negative.
 V. Miscellaneous:
  (1) Motility . . . negative.
  (2) Production of indol . . . +
  (3) Reduction of nitrate . . . negative
  (4) Production of hydrogen sulfide . . . +
  (5) Liquefaction of gelatin . . . +
  (6) Hydrolysis of esculin . . . negative
  (7) Adhering ability to the epithelium of oral mucous membrane . . . +++
  (8) Hemoagglutination . . . +++
 VI. Infection ability to animals: Induction of periodontitis . . . ± (determined with reference to the resorption of the alveolar bone).

The microorganisms which may be used as the source of the pilo component antigen of the present invention may be cultured in the conventional manner used for culturing various strains of the corresponding species. Thus, the culturing may be effected by using both synthetic and organic media, although the use of liquid media may be preferred for mass propagation. For example, the culturing may usually be effected at a temperature of 22°–39° C. (preferably about 37° C.) and at a pH of 5.0–8.0 (preferably about 7.4) under anaerobic conditions and usually continued, for example, for 24–72 hours.

Preferred media are exemplified as follows:

Medium A

Tryptocase peptone (1.7%, BBL), phyton peptone (0.3%, BBL), yeast extract (0.5%, Difco., U.S.A.), potassium phosphate dibasic (0.25%), sodium chloride (0.5%) and glucose (0.25%). pH=about 7.4.

Medium B

Medium A containing hemine (0.007%).

Medium C

Medium B containing hemine (0.005%) and vitamin K (0.0001%).

Medium A is suitable for Actinomyces and Actinobacillus, and media B and C are suitable for Bacteroides.

Preferred methods for the preparation of the vaccine of the present invention are exemplified as follows:

By culturing a microorganism at a temperature of 35°–37° C. and at a pH of 6.5–7.5 for 24–48 hours, a seed culture is obtained, which is then transferred to a main medium having the same composition for culturing 48–72 hours under similar conditions. After completion of the culturing, the number of the living cells in the cultured broth is usually more than about $10^8$ cells/ml. The cells are separated from the cultured broth, for example, by centrifugation (8000 r.p.m./20 min.) and suspended in a suitable buffer solution well known in the art such as, for example, a 0.1–1M acetic acid/sodium acetate buffer solution (pH 6.0–8.0), 0.01–0.75M phosphate buffered 1M saline solution (pH 6.5–8.0) and the like. A suitable non-ionic surfactant such as, for example, Triton X-100 (0.0001–0.1%; commercial product of Rohm and Haas, U.S.A.) may, if desired, be added.

The cell suspension is treated with ultrasonic waves (for example, 10–20 KHz/5–10 min.) to extract the desired pili component antigen.

The extracted solution containing the desired antigen is then fractionated and purified in a conventional manner, for example, by any of the following methods, alone or in combination: column chromatography, isoelectric point precipitation, partition precipitation using cold solvent such as ethanol and the like; membrane concentration, and salting-out using ammonium sulfate and the like.

If desired, it is also possible to treat the resultant solution with a suitable inactivating agent such as for example formalin (0.2-0.02%), followed by dialysis against a similar buffer solution to remove formalin.

The solution containing the antigen is diluted with a suitable buffer solution such as, for example, 0.1-1M phsophate buffered saline solution (pH 6.2-7.0) to adjust the protein N concentration to 5-50 μg/ml. To the diluted solution is added aluminum hydroxide as adjuvant at a final concentration of aluminum of about 100-500 μg/ml to adsorb the antigen. Instead of aluminum hydoxide, an equal amount of Fruend's complete adjuvant may, if desired, be used. To the mixture is added a suitable antiseptic agent such as thimerosal (0.005-0.1% w/v) to obtain an antigen solution of the present invention.

Instead of treatment with ultrasonic waves, it is also possible to add ammonium sulfate to the cell suspension at a concentration of about 20-70% (for example, 30%), followed by stirring to dissolve ammonium sulfate. Then the solution is allowed to stand at cold temperature, for example, 4° C. for 24-48 hours until the desired antigen is precipitated. The supernatant is collected and the precipitate is densely suspended in a suitable buffer solution such as, for example, a 0.05-0.5M phosphate buffered 1M saline solution (pH about 7.0-8.0), followed by dialysis against a similar buffer solution at cold temperature, for example, 4° C. The residual solution is centrifuged (e.g. 8000 r.p.m./20 min.) and the resultant extracted solution is fractionated and purified in a similar manner to that described above.

The thus-obtained antigen solution is diluted with a 0.5-1M (for example, 0.75M) phosphate-buffered saline solution (pH 6.2-7.0) to adjust the concentration of protein N to about 5-50 μg/ml. Then aluminum hydroxide is added to the mixture as adjuvant at a final concentration of aluminum of 200-500 μg/ml. A suitable antiseptic agent such as, for example, thimerosal (0.005-0.1% w/v) is added to the solution to obtain a vaccine solution of the present invention.

In order to obviate the denaturing of the pili component antigen of the present invention, the abovementioned procedure may advantageously be carried out at cold temperatures, for example, below 10° C. The vaccine thus-prepared may be preserved over extended period of time.

The dosage of the vaccine of the present invention may vary, depending upon various factors such as, for example, the types and symptoms of the periodontitis to be treated, the purpose of administration and the like. However, it is usually possible to administer the vaccine to humans at a daily dose of, for example, 0.2 to 2.0 ml/once by injection under the skin or into the muscle. Especially good results may be obtained by injection under the mucous membrane of the oral cavity. The immunization may be effected, for example, 2 to 5 times with an interval of 2 to 5 weeks. It is also possible, if desired, to adminster the vaccine continuously, for example, for 3 to 12 days.

By the use of the vaccine of the present invention, it is possible to inhibit the adherence of the wild strains of at least the corresponding species to the surfaces of teeth and the mucous membrane in the oral cavity, although the growth of the wild strains themselves may not be inhibited. It has been found that an antibody is produced in the body of the animal, in particular, in the saliva and serum, although no agglutinin is produced. By the action of the vaccine of the present invention, the inhibited wild strains are coagulated massively in the saliva, and may readily be removed in conventional manner, for example, by the use of dental paste, gargle and the like. The formation of dental plaque is advantageously inhibited. However, the growth of the virulent strains themselves may not be inhibited by the action of the present vaccine.

If desired, it is also possible to immunize a mammal with the vaccine of the present invention to produce an immunological antibody in the body of the mammal, from which the antibody is recovered and administered to humans and animals in a conventional manner.

In the following non-limiting examples for illustrating the invention, the culturing was effected at a temperature of about 35°-37° C. under anaerobic conditions in an atmosphere of nitrogen (90%) containing carbon dioxide (5%) and hydrogen (5), and as test animals, Golden hamsters, each group consisting of 10 animals, were used unless otherwise specified.

EXAMPLE 1

Preparation of *Actinomyces viscosus* Mutant Strain K-TL+ (FERM-BP-411)

Wild strains of *A. viscosus* were isolated from human periodontitis and cultured for 24 hours by using a Tryptocase soy broth [40 ml; pH 7.3; BBL] to obtain the cultured broth which was then centrifuged (8000 r.p.m/20 min.) to separate the cells. After washing three times with a 0.75M phosphate-buffered saline solution (each 200 ml; pH 7.0) by centrifugation (each 8000 r.p.m./20 min.), the cells were suspended in a similar buffer solution (pH 7.0; 10 ml) containing 0.2% of nitrogen mustard for 60-90 minutes at 37° C. until more than 90% of the cells were killed. The cells were washed three times by centrifugation (each 8000 r.p.m./20 min.) using a 0.75M phosphate-buffered saline solution (pH 7.0; each 200 ml) and the surviving cells were collected and smeared on a TYC agar plate medium (pH 7.4; 3 ml in a 9 cm dish) for culturing for 48 hours to form colonies. The culture was allowed to stand at room temperature for 24 hours and the resultant colonies were selected to obtain solid colonies having irregular margins and covered with abundant levan-type polysaccharides. If desired, the above-mentioned procedure may be repeated until a desired colony is obtained. The resultant colony was collected to obtain a pure culture of the desired strain.

EXAMPLE 2

Preparation of *Bacteroides gingivalus* Strain K-Bg-ml (FERM-BP-410)

Wild strains of *B. gingivalus* isolated from human pyorrhoea alveolaris were selected in view of a higher reactivity for hemoagglutination and a higher adhering ability to the epithelial cells of the mucous membrane of the oral cavity. The selected strains were cultured for 72 hours by using 10% blood agar plate media (pH 7.3; each 18 ml in a 9 cm dish) and then selected in view of their higher adhering ability. The selected strain was cultured for a period of 72-96 hours by using, on each occasion, a Tryptocase soy broth (pH about 7.2; 20 ml) to obtain the cultured broth which was then multiply diluted (×2) with a physiological solution of sodium chloride (pH 7.0) by the micro-titre plate method.

To each diluted solution (0.0025 ml), a 0.5% suspension of sheep red cells (0.0025 ml) was added with stirring, and the mixture was left at room temperature for 60-90 minutes. Where red cells separated over the entire bottom of the vessel, the cell sample was evaluated as being positive to the agglutination reaction. In this manner, a sample having a positive ability at the highest dilution was selected to obtain a pure culture. If desired, such a procedure may be repeated until a desired strain is obtained. The resultant strain exhibited stable characteristics when subcultured over extended period of time by using various known media.

EXAMPLE 3

Preparation of Vaccine (I)

*Actinomyces viscosus* Mutant Strain K-TL+ (FERM-BP-411) was cultured for 24 hours by using Medium A as hereinbefore defined (100 ml) to obtain a seed which was transferred to a main medium having the same composition (15000 ml) for culturing for 48 hours under similar conditions. Solid ammonium sulfate was added to the cultured broth at a 33% saturation. The broth was left at 4° C. overnight, followed by centrifugation (8000 r.p.m./20 min) to separate the cells. The cells were suspended in a 0.1M phosphate-buffered 1M saline (pH 7.0; 150 ml) and subjected to ultrasonic treatment (20 KHz/10 min.) while cooling with ice. The suspension was then centrifuged to remove the cell bodies and other impurities. Ammonium sulfate was added to the supernatant at a saturation of 60%, and the mixture was stirred to dissolve ammonium sulfate, followed by allowing to stand at a temperature of 4° C. for more than 24 hours. The precipitated fraction was collected and centrifuged (5000 r.p.m./20 min.). The thus-separated precipitate was dissolved in a 0.1M phosphate-buffered 1M saline solution (50 ml; pH 7.0) and subjected to dialysis against a similar buffer solution (2000 ml) at 4° C. for more than 24 hours.

The residual solution was centrifuged (8000 r.p.m./30 min.) to remove impurities. The resultant supernatant (about 60 ml) contained protein N of about 4-6 mg per ml, and was put into a cellophane tube and applied with Phecol 400 (commercial product of Pharmacia Fine Chemiclas AB., Seden) to reduce the amount to 1/10. The concetrated solution (each 1 ml) was, on each occasion, transferred on to each of 3 cellulose tubes, each containing 30 ml of a sucrose density gradient-solution (10-30%) and subjected at 4° C. to ultracentrifugation (35000 r.p.m./4 hours) by using a SW#25.1 Rotor (commercial product of Beckman Instrument Corp. U.S.A.). A Density Gradient Fractionator Type 1200 (commercial product of ISCO., U.S.A.) was used to collect fractions. Fractions having a specific weight of 1.38-1.42 and a sucrose density of about 14-18% contained the desired antigen, of which the protein N concentration was about 7-12 mg/ml.

EXAMPLE 4

Preparation of Vaccine (II)

*Bacteroides gingivalus* Strain K-Bg-ml (FERM-P BP-410) was cultured for 48 hours by using Medium B as hereinbefore defined (100 ml) to obtain a seed culture which was transferred to a main medium having the same composition (15000 ml) for culturing for 72 hours under similar conditions. The cultured broth was centrifuged (8000 r.p.m./20 min.) to separate the cells which were then suspended in a 0.1M phosphate-buffered 1M saline solution (pH 7.0; 200 ml). The extraction was effected at 4° C. with gentle stirring, and the extracted solution was centrifuged (10000 r.p.m./50 min.) to remove impurities. A 10% solution of zinc chloride was added dropwise to the resultant supernatant (about 200 ml) to a final concentration of zinc chloride of 1%. The pH of the solution was adjusted to 6.0 with 10% sodium carbonate solution, and the solution was left at 4° C. for 24 hours to form a precipitate which was collected by centrifugation (5000 r.p.m./5 min.) Crystals of disodium phosphate.12H$_2$O (150 g) was added to the thus-obtained precipitate. The mixture was well kneaded and then filtered with a glass filter under suction. Then a 10% solution of disodium phosphate (about 30 ml) was poured over the material for washing, and the resultant zinc phosphate was sucked out to obtain an extracted solution (about 90 ml). The above-mentioned two extracted solutions were combined together (about 300 ml in total). A saturated ammonium sulfate solution was added to the combined solutions to give a 60% saturation of ammonium sulfate. After removal of the supernatant, the precipitate was recovered by centrifugation (5000 r.p.m./5 min.) and dissolved in a 0.1M phosphate-buffered 1M saline solution (ph 7.0; 10 ml), followed by dialysis against a similar buffer solution (2000 ml) at 4° C. for more than 24 hours.

The residual solution was centrifuged (10000 r.p.m./30 min) to remove impurities. There was obtained a supernatant (about 30 ml) containing about 16 mg/ml of protein N, which was then purified in a similar manner to that described in Example 3. The desired antigen was present in the fractions having a specific weight of 1.36-1.41 and a sucrose of 12-16% by the sucrose density gradient ultracentrifugation. The combined active fractions exhibited a hemoagglutination ability of 1: more than 25600.

EXAMPLE 5

Preparation of Vaccine (III)

On each occasion, the fraction containing the pili component antigen originating from *Actinomyces viscosus* by the method of Example 3 or *Bacterioides gingivalus* by the method of Example 4 was diluted with a 0.75M phosphate-buffered saline solution (pH 6.2) to give a concentration of protein N of 20 μm/ml. The two thus-obtained antigen solutions were combined, to which aluminum hydroxide was added as adjuvant at a final concentration of aluminum of 200 μg per ml to adsorb the antigens. The pH of the combined antigen solution was adjusted to 6.2 and thimerosal (0.01% w/v) was added to the solution as antiseptic agent.

EXPERIMENT 1

Safety Test for Human Health

The vaccines prepared by the methods of Examples 3, 4 and 5 were respectively tested in the following manner. On each occasion, the dyeing test, the humidity test, the bacterial culturing test and the abnormal acute toxicity test were carried out according to "Test Methods for General Test Standard for Biological Medicine (1979)" issued by the Ministry of Public Welfare, Japanese Government. Nothing unusual was noted.

EXPERIMENT 2

Test for Adhesion to the Cells

The adhesion ability of the periodontitis-inducing strains to cells was tested by the method of Gibbons Van Houte [Infection and Immunity., April 1971, pages 567-573] in the following manner.

Epithelial cells collected from the mucous membrane of human oral cavity by using a spatula were washed well with Earl's buffer (pH 7.4) and suspended in a similar buffer solution at a concentration of about $10^5$ cells/ml. To it were then slowly added the cells of a virulent strain (about $10^6$ cells/ml) and the suspension was slowly shaken by using a rocking plate (about 1 r.p.m.). Then the suspension was transferred onto a membrane filter (15 μm; commercial product of Milipore Corpn., U.S.A.) and washed by pouring Earl's buffer solution under suction. The number of cells of the test strain adhered to the filter was counted by using a microscope.

EXPERIMENT 3

(1) The immunological activity of the vaccine prepared by the method of Example 5 (mixed vaccine) was investigated by using Golden hamsters 21 days old as test animals in the following manner.

*A. viscosus* Mutant Strain K-TL+ and *B. gingivalus* Strain K-Bg-ml were respectively cultured for 24 hours by using Medium A and Medium B as hereinbefore defined (each 10000 ml). After completion of the culturing, each cultured broth was centrifuged (8000 r.p.m./20 min.) to separate the cells, and the separated cells of two strains were added to a physiological solution of sodium chloride (pH 7.0) to obtain a cell suspension containing both cells at a concentration of about $10^8$ cells/ml for each. The cell suspension was administered to each test animal (into the buccal cavity) at a daily dose of 0.2 ml every day between the 21st and 35th day after birth and then at the same daily dose once per week. During the test period, each animal was bred with a cariogenic diet (Diet 2000, commercial product of Funabashi Nojo, Japan; 10-30 g/day) and deionized water. The mixed vaccine of the present invention was administered to each test animal by injection under the skin of the buccal cavity. The administration was effected at a daily dose of 0.2 ml on the 21st and 28th days and 0.4 ml on the 35th day after birth. All animals were bred for 80 days. After completion of breeding, all animals were anesthetized with pentabarbital and abdominally injected with pilocarpin HCl (0.75%; each 0.1 ml/100 g of body weight). The saliva was collected from each animal which was then killed by cardiac puncture. The maxilla was removed from each animal and treated in an autoclave at about 121° C. for 1-2 minutes to remove the soft part. The remaining part was washed with water and dried to obtain a sample of its teeth. The control animals were treated in a similar manner to that described above without administration of the mixed vaccine of the present invention.

During the test period, samples of oral floras were from time to time collected from the surfaces of the upper and lower molars of each animal. On each occasion, the thus-collected sample was cultured for 72 hours by the use of a 10% blood agar plate medium, Bacteroides agar plate medium and TYC agar plate medium. On each occasion, after completion of the culturing, the cultured broth was allowed to stand at room temperature for 24 hours to investigate the colonial and serological characteristics of the grown cells.

(2) In order to investigate the differences of the resorption of the alveolar bone between the test animals and control animals, the resorption which occurred in each animal of the test group and control group was determined by Tsukiyama et al method [Journal of Oral Health, Vol. 28, No. 3, page 149 (1978) in Japanese version] as follows:

Each sample of the maxilla of the test animala and the control animals was dyed with a 20% silver nitrate solution for 5 minutes, and the an ocular micrometer (5×4) was used to measure microscopically the distance between the enamel-cementum junction and the edge of the alveolar bone of each bone sample.

(3) Antibodies produced in the saliva and serum of each animal were assayed by the quantative agglutination test using the micro-titre plate method in a conventional manner, and the relation between the antibodies produced in the test animals and the antibodies produced in the control animals was investigated by the adherence inhibition test and the precipitation reaction in the gel in the following manner.

The antigens used for the agglutination test were prepared as follows: *A. viscosus* Mutant Strain K-TL+ and *B. gingivalus* Atrain K-Bg-ml were independently cultured for 24 hours by using each Todd Heuwitt broth (pH about 7.8; each 200 ml; BBL). On each occasion, after completion of the culturing, the cultured broth was centrifuged (8000 r.p.m./20 min.) to separate the cells from the cultured broth. The cells were then inactivated by allowing them to stand at 37° C. for 12 hours in a physiological solution of sodium chloride (pH 7.0; 100 ml) containing 0.2 mM glutaraldehydes and separated by centrifugation (8000 r.p.m./20 min.). The cells were suspended in a physiological solution of sodium chloride (pH 7.0) at a concentration having an optical density of 0.50 at 550 nm to obtain an antigen-containing solution which was then subjected to multiple dilution (×2) with a similar saline solution and divided into small fractions (each 0.025 ml) by the micro-titre method.

To each diluted solution of the saliva or serum obtained from the test animal (0.025 ml) was added an antigen solution (each 0.025 ml) to carry out the reaction at 37° C. for 4 hours. The reaction mixture was allowed to stand at 5° C. overnight and the results were investigated with unaided eyes.

The adhering ability was tested in the following manner:

On each occasion, the saliva or serum of the test animal was diluted (×10) with a TYC medium (pH 7.2) and the diluted material was sterily filtered by using a membrane filter (0.45μ; commercial product of Milipore Corp., U.S.A.), followed by dilution (×2) with a similar medium. 0.01 ml of the cultured broth was then added to each diluted material. The broth was obtained by culturing *Actinomyces viscosus* Mutant Strain K-TL+ or *Bacteroides gingivalus* Strain Bg-ml for 24 hours by using each Todd Heuwitt broth (each 10 ml; pH about 7.8). The cultured broth was inoculated for culturing for 24 hours to investigate the adherence of the cultured cells to tube wall.

The pili component antigens prepared by the methods of Examples 3 and 4 were used for the precipitation in the gel test effected according to the double diffusion test method. The gel used was prepared by Goldman et al method [J. Cell. Biol., Vol. 78, 426–440 (1980)] using 0.15M sodium chloride, 0.5% Triton X-100 (commercial product of Rohm and Haas, U.S.A.), 0.1% lauryl sodium sulfate and 1% agarose (Sigma, U.S.A.).

The following Table 1 indicates the results of the test of protection against infection. The following may be noted:

adhered cells to the animals of Group 2 was very low or not detectable. The adherence of B. gingivalus to all test animals was investigated. However, in some cases, the adherence was not found, and even when adhered, the adherence was not necessarily good. At the last state of the test, a relatively large number of cells was found in certain animals of Group 1.

TABLE 1

| Animal | | Res. | | Antibody titres | | | | | |
|---|---|---|---|---|---|---|---|---|---|
| | | | | Agg | | Adh | | Pre | |
| Group | W | UJ | LJ | A | B | A | B | A | B |
| 1 | 128 | 45.5 | 65.3 | *16–32<br>**16–32 | <4 | 8–16 | 8–64 | + | + |
| 2 | 113 | 95.9 | 100.4 | <4–8<br><4 | <4<br><4 | <2–4 | <2–8 | —~+<br>—~+ | —<br>—~+ |
| 3 | 133 | 32 | 32 | <4<br><4 | <4<br><4 | <2 | <2 | —<br>— | —<br>— |

Notes:
Animal Group:
1—periodontitis - no vaccine
2—periodontitis - with vaccine
3—untreated
W—Body weight in average (g);
Res—Resorption of the alveolar bone in average (%);
UJ—Upper jaw; LJ—lower jaw;
Agg—agglutination titre; Adh—adherence inhibition;
Pre—Precipitation in gel;
A—in the serum; B—in the saliva;
*A. viscosus
**B. gingivalus (a) A stronger resorption of the alveolar bone is found in each animal of Group 1 (periodontitis was induced and the present vaccine was not administered for immunization). In each animal of Group 2 (periodontitis was induced and the present vaccine was administered for immunization), the inhibition of the resorption of the alveolar bone was significant. No significant difference was observed between the animals of Group 2 and Group 3 (untreated).

(b) With regard to the antibody titres, certain animals of Group 2 (induced and immunized) exhibited low agglutinin titres in the serums. However, the corresponding titres in the saliva were lower than the titres in the serums.

(c) With regard to the adherence of *Actinomyces viscosus*, the inhibition effect was found in each animals of Group 2 (immunized group) and the activities in the saliva were stronger then the activities in the serum. Although such activities were noted in certain animals of Group 1 (induced without immunization), they were however lower than the corresponding titres found in the animals of Group 2.

(d) In each of the animals of Group 2 (immunized group), the precipitin reactions in gel using two pili component antigens were positive in the saliva and serum, although the results could hardly be determined in the animals of other test groups.

(e) With regard to the adherence of two test strains to the animals of Groups 1 (induced without immunization) and 2 (immunized and infected), although the adherence of A. viscosus was detectable in all animals during the entire test period. However, the number of

We claim:

1. A vaccine for preventing or inhibiting periodontitis induced or deteriorated by the action of oral microorganisms selected from the genera Actinomyces, Bacteriodes and Actinobacillus, which comprises as active ingredient at least one antigen which is obtained by dispersing the cells of at least one of said oral microorganism in a hypertonic buffer solution containing sodium chloride and isolating the desired antigen from pili-like structures on the surface layer of said cells at a low temperature sufficient to obviate the denaturing of said antigen.

2. The vaccine of claim 1 wherein the isolating is effected by extraction carried out at a temperature of less than 10° C.

3. The vaccine of claim 1 wherein the microorganism is selected from the genus *Bacteriodes gingivalis*.

4. The vaccine of claim 1, wherein the microorganism is selected from the genus *Actinobacillus actinomycetem comitans*.

5. The vaccine of claim 1, wherein the microorganism is *Bacteriodes gingivalis* Strain K-Bg-m1 (FERM-BP 410).

6. The vaccine of claim 1 wherein the microorganism is selected from the group consisting of *Actinomyces viscosus* and mutant strains thereof.

7. The vaccine of claim 1 wherein the microorganism is selected from the group consisting of *Actinomyces naeslundii*.

8. The vaccine of claim 1 wherein the microorganism is selected from the group consisting of *Actinomyces viscosus* Mutant Strain K-TL+ (FERM-BP 411).

* * * * *